United States Patent
Loebermann et al.

(10) Patent No.: US 7,557,218 B2
(45) Date of Patent: Jul. 7, 2009

(54) HYDRATES OF OPTIONALLY SUBSTITUTED 2-(2-PYRIDINYL) METHYLTHIO-1H-BENZIMIDAZOLES AND PROCESS FOR THE PRODUCTION THEREOF

(75) Inventors: Hartmut Loebermann, Aachen (DE); Karl-Heinz Caster, Eschweiler (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 12/169,813

(22) Filed: Jul. 9, 2008

(65) Prior Publication Data

US 2008/0269497 A1    Oct. 30, 2008

Related U.S. Application Data

(60) Division of application No. 10/772,033, filed on Feb. 4, 2004, now Pat. No. 7,435,825, which is a continuation of application No. PCT/EP02/08867, filed on Aug. 8, 2002.

(30) Foreign Application Priority Data

Aug. 17, 2001  (DE) ................. 101 40 492

(51) Int. Cl.
*C07D 401/12*   (2006.01)
(52) U.S. Cl. .................................. 546/273.7
(58) Field of Classification Search ............... 546/273.7
See application file for complete search history.

(56) References Cited

FOREIGN PATENT DOCUMENTS

| EP | 0 005 129 | 4/1979 |
|---|---|---|
| EP | 0 074 341 | 8/1982 |
| EP | 0 254 588 | 7/1987 |
| EP | 0 899 268 | 3/1999 |
| WO | 97/29103 | 8/1997 |
| WO | 98/21201 | 5/1998 |
| WO | 98/50361 | 11/1998 |
| WO | 00/09497 | 2/2000 |
| WO | 00/78729 | 12/2000 |

OTHER PUBLICATIONS

Berstein, "Polymorphism in, etc.," Oxford: Clarendon Press, 2002, p. 273.
Brittain et al, "Polymorphism in Pharmaceutical Solids", NY: Marcel Dekker, Inc., 1999, pp. 1-2, 185.
Muzaffar et al, "Polymorphism and Drug Availability, etc.", J of Pharm. (Lahore), 1979, 1(1), 59-66.
Concise Encyclopedia Chemistry, NY: Walter de Gruyter, 1993, 872-873.
Bernstein et al., "Polymorphism in Molecular Crystals", Oxford: Clarendon Press, 2002, pp. 117, 118 and 272.
Davidovitch et al., "Detection of Polymorphism, etc.," American Pharmaceutical Review, IN: Russell Pub., 2004, 7 (1), pp. 10, 12, 14, 16 and 100.
B. Kotar-Jordan et al, "Solid State Characterization of K-1252"; The Second Central European Symposium on Pharmaceutical Technology, 1997, pp. 228 & 289.
U S Pharmacopia, 1995, pp. 1843-1844.
Brittain et al, "Polymorphism in Pharmaceutical Solids", NY: Marcel Dekker, Inc., 1999, pp. 125-181 and 279-330.
Hashimoto et al, "Process for producing, etc.," CA 136: 5990, 2001.

*Primary Examiner*—Patricia L Morris
(74) *Attorney, Agent, or Firm*—Norris, McLaughlin & Marcus, PA

(57) ABSTRACT

The invention relates to crystals from optionally substituted 2-(2-pyridinyl)methylthio-1H-benzimidazole hydrates and to a method for the production thereof.

9 Claims, No Drawings

HYDRATES OF OPTIONALLY SUBSTITUTED 2-(2-PYRIDINYL) METHYLTHIO-1H-BENZIMIDAZOLES AND PROCESS FOR THE PRODUCTION THEREOF

This application is a division of U.S. patent application Ser. No. 10/772,033 filed Feb. 4, 2004, now U.S. Pat. No. 7,435,825, which is a continuation of PCT/EP02/08867 filed Aug. 8, 2002, which claims priority of DE 101 40 492.1 filed Aug. 17, 2001.

The invention relates to crystals of optionally substituted 2-(2-pyridinyl)methylthio-1H-benzimidazole hydrates and to a process for the production thereof.

It is known that 2-(2-pyridinyl)methylthio-1H-benzimidazole compounds, such as for example pyrmetazole (5-methoxy-2-[(4-methoxy-3,5-dimethyl-2-pyridinyl)methylthio]-1H-benzimidazole) are the final intermediate for the production of antiulceratives, in particular omeprazole or lanzoprazole. Such an antiulcerative is produced by converting the sulfide compound, such as for example pyrmetazole, by oxidation into the corresponding sulfinyl compound, such as for example omeprazole.

Substituted 2-(2-pyridinyl)methylthio-1H-benzimidazoles are conventionally produced under alkaline conditions in organic solvents by reaction of mercaptobenzimidazole compounds, such as for example 5-methoxy-2-mercaptobenzimidazole, with reactive pyridine compounds, such as for example 2-chloromethyl-3,5-dimethyl-4-methoxypyridine.

EP 0 005 129 A describes the production of 2-(2-pyridinyl) methylthio-1H-benzimidazole compounds by reacting suitable mercaptobenzimidazole compounds with chloromethylpyridine compounds. The reaction proceeds in an organic solvent, such as for example ethanol, in the presence of a base, such as for example sodium hydroxide.

Once the reaction is complete, the resultant common salt is separated, the solvent removed under a vacuum and the monohydrochloride of the compound is caused to crystallise by means of concentrated hydrochloric acid in acetone and is purified. The yields achieved in this process are barely satisfactory. Moreover, the hydrochloride must be converted back into the base before the oxidation reaction.

EP 0 074 341 A describes the production of 2-(2-pyridinyl)-methylthio-1H-benzimidazole compounds by reacting suitable mercaptobenzimidazole compounds with chloromethylpyridine compounds in the presence of sodium hydroxide. Methanol is used as the solvent. Once the reaction is complete and water has been added, the 2-(2-pyridinyl)methylthio-1H-benzimidazole compound is purified by repeated extraction with methylene chloride and recrystallisation from acetonitrile. The solvents used in this process are hazardous to the environment. Moreover, due to the repeated extraction steps, the process is time-consuming.

EP 0 899 268 A2 describes inter alia the production of 2-[2-(4-chloro-3,5-dimethylpyridyl)methylthio]-5-methoxy-1H-benzimidazole by the reaction of suitable starting compounds in tetrahydrofuran and in the presence of sodium hydroxide solution. Once the reaction is complete and water has been added, the stated compound is isolated by repeated extraction with methylene chloride and evaporation of the solvent. The compound is obtained as a viscous oil. Disadvantageous features of this process are the use of a solvent which is hazardous to the environment and the time-consuming isolation by repeated extraction. Moreover, the product in the form of a viscous oil is more technically demanding to handle than a crystalline compound.

The object of the present invention was accordingly to provide the optionally substituted 2-(2-pyridinyl)-methylthio-1H-benzimidazoles in a form which is stable and can be stored and is obtained by straightforward processing steps in elevated yields and in high purity, wherein it is possible to use solvents which are more environmentally friendly and present a reduced hazard to health.

The object is achieved by the provision of crystals of optionally substituted 2-(2-pyridinyl)methylthio-1H-benzimidazole hydrates of the structural formula I,

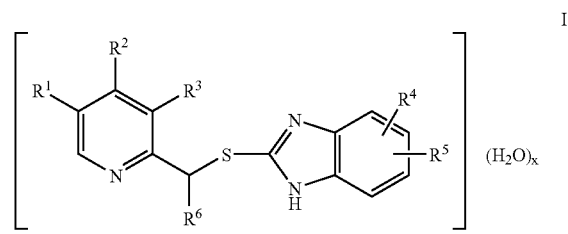

in which $R^1$, $R^2$ and $R^3$, identical or different, denote hydrogen, C1-C8 alkyl, C3-C8 cycloalkyl, C2-C8 fluoroalkyl or C1-C8 alkoxy, $R^4$ and $R^5$, identical or different, denote hydrogen, C1-C8 alkyl, C3-C8 cycloalkyl, $CH_2$—C3-C8 cycloalkyl, C1-C8 alkoxycarbonyl, C1-C8 alkoxy, C1-C8 fluoroalkoxy, $CF_3$, C2-C8 fluoroalkyl or —C(O)O—C1-C8 alkyl and $R^6$, identical or different, denotes hydrogen or C1-C2 alkyl and x denotes 0.5-2.

$R^1$-$R^6$ preferably have the following meaning $R^1$, $R^2$ and $R^3$, identical or different, denote hydrogen, C1-C3 alkyl or C1-C3 alkoxy, $R^4$ and $R^5$, identical or different, denote hydrogen, C1-C3 alkoxy, C1-C3 fluoroalkoxy and $R^6$, identical or different, denotes hydrogen.

Particularly preferred compounds are those in which $R^1$ denotes a methyl group, $R^2$ a methoxy group, $R^3$ a methyl group, $R^4$ hydrogen, $R^5$ a methoxy group in position 5 and $R^6$ hydrogen or in which $R^1$ denotes hydrogen, $R^2$ and $R^3$ in each case denote a methoxy group, $R^4$ denotes hydrogen, $R^5$ a difluoromethoxy group in position 5 and $R^6$ hydrogen.

The present invention also provides a process for the isolation of a compound according to formula I from a reaction medium, in which the compound is present as a free base, in elevated yields, wherein a water-miscible, organic solvent present in the reaction medium is at most partially removed and water is added to the reaction medium at a temperature of below 40° C., preferably of 20-25° C., in quantities of at least 55 wt. %, preferably at least 70 wt. %, particularly preferably up to 75 wt. %, relative to the reaction medium, and the consequently formed hydrates are separated as crystals and optionally purified in conventional manner and dried. When removing the organic solvent, care should be taken to ensure that its concentration does not fall below the solubility limit for the compound of the formula I.

The compounds of the formula I are preferably to be separated from a reaction medium which is obtained by reacting a thiol compound of the formula II

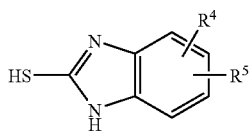

in which $R^4$ and $R^5$ have the above-stated meaning, with a reactive pyridine compound of the formula III,

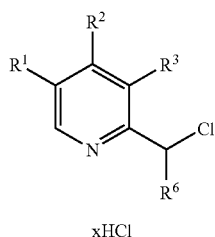

in which $R^1$, $R^2$, $R^3$ and $R^6$ have the above-stated meaning, in a water-miscible, organic solvent in the presence of a base. Suitable bases for this reaction are preferably sodium and/or potassium hydroxide. This reaction preferably proceeds with several hours' refluxing. The reaction may be performed continuously or discontinuously.

The compound of the formula I may be obtained from the reaction medium, which contains the compound as a free base, by at most partial removal of the water-miscible, organic solvent and by addition of water in quantities of at least 55 wt. %, preferably at least 70 wt. %, particularly preferably up to 75 wt. %, relative to the reaction medium, at a temperature of below 40° C., preferably of 20-25° C. When removing the organic solvent, care should be taken to ensure that its concentration does not fall below the solubility limit for the compound of the formula I.

The sodium and/or potassium chloride arising from the neutralisation of the added base may be separated beforehand by suitable means, for example by filtration, or be dissolved by the addition of water on formation of the hydrate. The hydrates of the 2-(2-pyridinyl)methylthio-1H-benzimidazoles may optionally be further purified and dried.

Thiol compounds of the formula II may be purchased commercially. Reference is also made to EP 0 254 588, EP 0 005 129 and EP 0 074 341 for a description of the synthesis thereof, the corresponding description hereby being introduced as part of the present disclosure. Reference is made to WO 98/50361 and WO 97/29103 for a description of the synthesis of the reactive pyridine compounds of the formula III, the corresponding description hereby being introduced as part of the present disclosure.

The present invention also provides a process for the production of a compound according to the formula I, in which the unhydrated compound of the formula I is dissolved in a water-miscible, organic solvent or solvent mixture and is caused to crystallise by addition of water in quantities of at least 55 wt. %, preferably at least 70 wt. %, particularly preferably up to 75 wt. %, relative to the reaction medium, at a temperature of below 40° C., preferably of 20-25° C., and the consequently formed crystals of the compound according to the formula I are separated, optionally purified and dried.

The water-miscible, organic solvents used in the above-stated reactions are preferably highly volatile solvents, such as aliphatic alcohols, aprotic solvents or ketones, particularly preferably methanol, ethanol, propanol, butanol, dimethylformamide, dimethyl sulfoxide, tetrahydrofuran or acetone, or mixtures of at least two of these solvents.

The present invention also provides a process for the purification of crystals of a compound according to the formula I, in accordance with which the hydrate to be purified is washed at least once with water and/or a solvent/water mixture, preferably an alcohol/water mixture and/or a ketone/water mixture, and is then dried under a vacuum at below the melting point of the hydrates.

The crystals according to the invention of the optionally substituted 2-(2-pyridinyl)methylthio-1H-benzimidazole hydrates of the formula I are stable and can be stored. They are straightforward to produce, isolate and purify and may be used directly for oxidation to yield the corresponding sulfinyl compounds, which are used as an antiulcerative. With the assistance of the process according to the invention, it is possible to produce crystals of optionally substituted 2-(2-pyridinyl)-methylthio-1H-benzimidazole hydrates of the formula I in elevated yields and in high purity, wherein it is possible to use solvents which are more environmentally friendly and present a reduced hazard to health.

The following Examples illustrate the invention without limiting it thereto.

EXAMPLES

Example 1

0.05 mol of 2-mercapto-5-methoxybenzimidazole were added to a solution of 0.11 mol of sodium hydroxide in 90 ml of ethanol. 0.05 mol of 2-chloromethyl-3,5-dimethyl-4-methoxy-pyridine hydrochloride were added to the solution and the reaction mixture was refluxed for 14 hours. 270 ml of water were then added at room temperature (25° C.), wherein the hydrates of 5-methoxy-2-[3,5-dimethyl-4-methoxypyridinyl)-methylthio]-1H-benzimidazole crystallised. The whitish crystalline product was separated, washed with water and dried under a vacuum.

Yield: 95% relative to theoretical yield (15.6 g).

The purity of the compound was determined by HPLC and was 99.7%.

Example 2

0.1 mol of 2-mercapto-5-methoxybenzimidazole were added to a solution of 0.22 mol of sodium hydroxide in 250 ml of methanol. 0.1 mol of 2-chloromethyl-3,5-dimethyl-4-methoxypyridine hydrochloride were added to the solution and the reaction mixture was refluxed for 16 hours. 80 ml of solvent were then removed under a vacuum and 400 ml of water were then added at room temperature (25° C.), wherein the hydrates of 5-methoxy-2-[3,5-dimethyl-4-methoxy-pyridinyl)methylthio]-1H-benzimidazole crystallised. The whitish crystalline product was separated, washed with methanol/water and dried under a vacuum.

Yield: 92.5% relative to theoretical yield (30.3 g).

The purity of the compound was determined by HPLC and was 99.5%.

Example 3

0.1 mol of pyrmetazole hydrochloride (the compound was produced according to details stated in Example 31 of EP 0

005 129) were dissolved in 60 ml of water, then 60 ml of ethanol were added, the pH value of the solution was adjusted to greater than pH 7 with a 5 N sodium hydroxide solution and a further 120 ml of water were added at room temperature (25° C.), wherein the hydrates of the pyrmetazole crystallised. The whitish crystalline product was separated, washed with water and dried under a vacuum.

Yield: 90.2% relative to theoretical yield (29.5 g).

The purity of the compound was determined by HPLC and was 99.9%.

Example 4

Pyrmetazole, in the form of a solution in methylene chloride, was first produced according to Example 26 of EP 0 899 268. Methylene chloride was removed under a vacuum from such a solution, which contained 0.1 mol of pyrmetazole. The residual oil was dissolved in 210 ml of ethanol and caused to crystallise as the hydrate of pyrmetazole by the addition of 630 ml of water. The whitish crystalline product was separated, washed with water and dried under a vacuum.

Yield: 96% relative to theoretical yield (31.5 g).

The purity of the compound was determined by HPLC and was 99.8%.

What is claimed is:

1. A process for isolating crystals of an optionally substituted 2-(2-pyridinyl)methylthio-1H-benzimidazole hydrate of formula I:

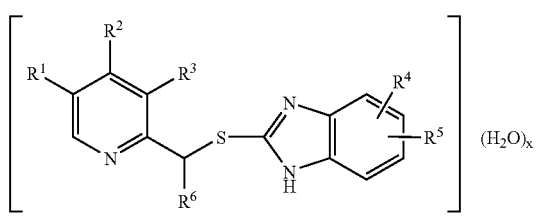

in which

R$^1$, R$^2$ and R$^3$, identical or different, denote hydrogen, a C1-C8 alkyl, C3-C8 cycloalkyl, C2-C8 fluoroalkyl or C1-C8 alkoxy moiety, R$^4$ and R$^5$, identical or different, denote hydrogen, a C1-C8 alkyl, C3-C8 cycloalkyl, CH$_2$—C3-C8 cycloalkyl, C1-C8 alkoxycarbonyl, C1-C8 alkoxy, C1-C8 fluoroalkoxy, CF$_3$—, C2-C8 fluoroalkyl or C(O)O—C1-C8 alkyl moiety, and R$^6$ denotes hydrogen or a C1-C2 alkyl moiety and x means 0.5-2, said process comprising:

a) providing a reaction medium comprising (i) the free base of the structural formula:

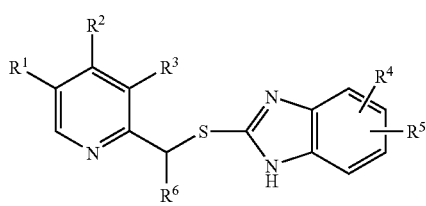

wherein R$^1$-R$^6$ have the meaning given above; and (ii) a water-soluble, organic solvent;

b) at most partially removing the water-soluble, organic solvent present in the reaction medium;

c) adding water to the reaction medium at a temperature of below 40° C. in quantities of at least 55 wt. % of water, relative to the weight of the reaction medium, to form hydrates;

d) separating the hydrates formed as crystals; and e) optionally purifying the crystals.

2. A process according to claim 1, wherein the water is added in quantities of at least 70 wt. % relative to the weight of the reaction medium.

3. A process according to claim 1, wherein the water is added in quantities of up to 75 wt. % relative to the weight of the reaction medium.

4. A process according to claim 1, wherein the water is added at a temperature of 20-25° C.

5. A process according to claim 1, wherein the free base in the reaction medium was prepared by a process comprising reacting a thiol-compound of the formula II:

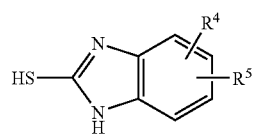

with a reactive pyridine compound of the formula III:

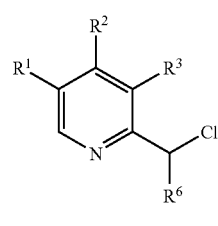

xHCl in presence of at least one base.

6. A process according to claim 5, wherein the base is at least one member selected from the group consisting of sodium and potassium hydroxide.

7. A process according to claim 1, wherein the free base is initially dissolved in a water-miscible, organic solvent.

8. A process according to claim 1, wherein the water-miscible, organic solvent is an aliphatic alcohol, or an aprotic solvent, or a ketone, or a mixture of at least two of these solvents.

9. A process according to claim 1, wherein the crystals are purified by washing with at least one of water and a solvent/water mixture.

* * * * *